(12) United States Patent
Stephens et al.

(10) Patent No.: US 11,058,159 B2
(45) Date of Patent: Jul. 13, 2021

(54) GARMENT FOR POST-OPERATIVE PAIN AND WOUND MANAGEMENT

(71) Applicant: THE MARENA GROUP, LLC, Lawrenceville, GA (US)

(72) Inventors: Jeffrey Dan Stephens, Atlanta, GA (US); Terrell Douglas Abney, Atlanta, GA (US); Linda Marie Burhance, Newtown, CT (US); Jeffrey Robert Cellini, Peachtree City, GA (US)

(73) Assignee: THE MARENA GROUP, LLC, Lawrenceville, GA (US)

( * ) Notice: Subject to any disclaimer, the term of this patent is extended or adjusted under 35 U.S.C. 154(b) by 13 days.

(21) Appl. No.: 15/990,975

(22) Filed: May 29, 2018

(65) Prior Publication Data

US 2018/0338551 A1 Nov. 29, 2018

Related U.S. Application Data

(60) Provisional application No. 62/511,589, filed on May 26, 2017.

(51) Int. Cl.
*A41D 13/12* (2006.01)
*A61F 5/03* (2006.01)
(Continued)

(52) U.S. Cl.
CPC ............ *A41D 13/1245* (2013.01); *A61F 5/03* (2013.01); *A41B 2400/32* (2013.01); *A41C 1/08* (2013.01); *A61F 5/4408* (2013.01)

(58) Field of Classification Search
CPC ............ A41D 13/1245; A41D 13/1236; A41D 13/129; A41D 13/1281; A41D 13/0012;
(Continued)

(56) References Cited

U.S. PATENT DOCUMENTS 3,378,013 A    4/1968   Bruno
3,529,307 A *   9/1970   Belson ............... A41D 13/0012
                                                                            2/94

(Continued)

OTHER PUBLICATIONS

Omer Cordura Belt Pocket for Light/Weights, URL: https://www.scubastore.com/scuba-diving/omer-cordura-belt-pocket-for-light-weights/1245552/p, Jan. 11, 2017.
(Continued)

*Primary Examiner* — Alissa L Hoey
*Assistant Examiner* — Patrick J. Lynch
(74) *Attorney, Agent, or Firm* — Barnes & Thornburg LLP; Jason Bernstein

(57) ABSTRACT

A garment for wearing post-surgery, comprising first and second panel portions constructed of an elastic material, a closure mechanism for detachably attaching the edges of the panel portions, and, an elastic support band associated with either the upper or bottom area of the panel portions. The garment may further include at least one retention strip of material associated in at least one place on the first or second panel portions. At least one retention member is adapted to removably attach to the retention strip. At least one pouch that can hold a drainage bulb, monitoring device, or other item, may also be removably attached to the retention strip. The garment may be constructed as a vest, girdle, leg sleeve, or other form.

16 Claims, 4 Drawing Sheets

(51) Int. Cl.
*A41C 1/08* (2006.01)
*A61F 5/44* (2006.01)

(58) Field of Classification Search
CPC .... A41D 13/0007; A41D 27/08; A41D 1/002; A41D 13/1254; A41D 13/1263; A61F 5/4408; A61F 5/449; A41C 3/0064
USPC ...................................................... 2/102, 69
See application file for complete search history.

(56) References Cited

U.S. PATENT DOCUMENTS

| | | | |
|---|---|---|---|
| 5,257,956 A | 11/1993 | Ewen | |
| 5,378,192 A | 1/1995 | Darmante | |
| 6,055,668 A * | 5/2000 | Gros | A41D 13/1245 2/69 |
| 6,936,021 B1 | 8/2005 | Smith | |
| 7,396,272 B1 | 7/2008 | Newlen | |
| 8,337,275 B2 | 12/2012 | Martins-Crawbuck et al. | |
| 8,562,388 B2 | 10/2013 | Izzo et al. | |
| 8,944,974 B2 | 2/2015 | Foster | |
| 9,161,574 B2 | 10/2015 | Swendseid et al. | |
| 9,545,124 B1 * | 1/2017 | Thompson | A41C 3/0064 |
| 9,591,880 B2 | 3/2017 | Lee et al. | |
| 9,951,880 B2 | 4/2018 | Thomas et al. | |
| 2006/0206978 A1 * | 9/2006 | Hilton | A41D 1/215 2/104 |
| 2010/0121288 A1 * | 5/2010 | Timmons | A61F 5/4408 604/327 |
| 2011/0034889 A1 * | 2/2011 | Smith | A61F 5/449 604/327 |
| 2013/0171911 A1 * | 7/2013 | Swendseid | A41C 3/0057 450/85 |
| 2015/0080860 A1 | 3/2015 | Farrell | |
| 2015/0099420 A1 | 4/2015 | Reinhard | |
| 2015/0296896 A1 * | 10/2015 | Laguna | A61F 13/14 450/58 |
| 2016/0066624 A1 * | 3/2016 | Blackwell | A41C 3/0064 450/58 |
| 2016/0143424 A1 | 5/2016 | Stephens et al. | |
| 2016/0213886 A1 * | 7/2016 | DiGiorgi | A61F 5/4408 |
| 2016/0367021 A1 * | 12/2016 | Moreau | A45F 5/00 |
| 2017/0056630 A1 * | 3/2017 | Fee | A61M 25/02 |
| 2017/0202274 A1 | 7/2017 | Blackwell | |
| 2020/0077718 A1 * | 3/2020 | Thompson | A41C 3/0064 |

OTHER PUBLICATIONS

Search Report for International Patent Application No. PCT/US2018/34837, dated Oct. 15, 2018.
International Preliminary Report on Patentability for International Application No. PCT/US2018/034837; dated Mar. 12, 2020.

* cited by examiner

GARMENT FOR POST-OPERATIVE PAIN AND WOUND MANAGEMENT

CROSS-REFERENCE TO RELATED APPLICATION

This application claims benefit of U.S. provisional patent application No. 62/511,589, filed May 26, 2017, entitled VEST GARMENT FOR POST-OPERATIVE PAIN AND WOUND MANAGEMENT, and commonly assigned to the assignee of the present application, the disclosure of which is incorporated by reference in its entirety herein.

FIELD

The present disclosure relates, in exemplary embodiments, to an elastic garment suitable for use after surgery, for example, cardiac-related surgery, for pain and wound management.

BACKGROUND

After surgery the patient typically must, or should, wear a post-surgery compression garment to help speed recovery and improve comfort. Frequently, a drainage tube inserted near the incision or proximal area is needed to drain fluid from the surgery area. The tube usually drains into a drainage bulb. Both the tube and the bulb are essentially "attached" to the patient, and carrying both around can be cumbersome and embarrassing. Additionally, the tube may occasionally need to be repositioned. It would be desirable to have a garment worn post-surgery that can accommodate and retain both the tube and the bulb (and other items). It would also be desirable for such a garment to accommodate adjusting the position of the tube and/or pouch around the garment as needed to maintain comfort. It would also be desirable for such a garment to have desirable compression and breathability characteristics to help with healing.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

In one exemplary embodiment, a garment for post-surgical use in pain and wound management is provided, comprising: (a) a first panel portion including an edge, a second panel portion including an edge, the first and second panel portions having an upper portion and a bottom portion, the first and second panel portions being made of an elastic material; (b) a front closure adapted for removably joining at least a portion of the first and second panel portion edges; (c) an elastic support band associated with either the upper portion or the bottom portion; and, (d) at least one retention strip associated with the support band. The garment may further include at least one retention member removably attachable to a portion of the retention strip. The garment may further include at least pouch removably attachable to a portion of the retention strip.

Other features will become apparent upon reading the following detailed description of certain exemplary embodiments, when taken in conjunction with the appended claims.

BRIEF DESCRIPTION OF THE DRAWINGS

The drawings disclose exemplary embodiments in which like reference characters designate the same or similar parts throughout the figures of which.

DETAILED DESCRIPTION

Unless otherwise indicated, the drawings are intended to be read (for example, cross-hatching, arrangement of parts, proportion, degree, or the like) together with the specification, and are to be considered a portion of the entire written description of the invention. As used in the following description, the terms "horizontal", "vertical", "left", "right", "up" and "down", "upper" and "lower" as well as adjectival and adverbial derivatives thereof (for example, "horizontally", "upwardly", or the like), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 1:
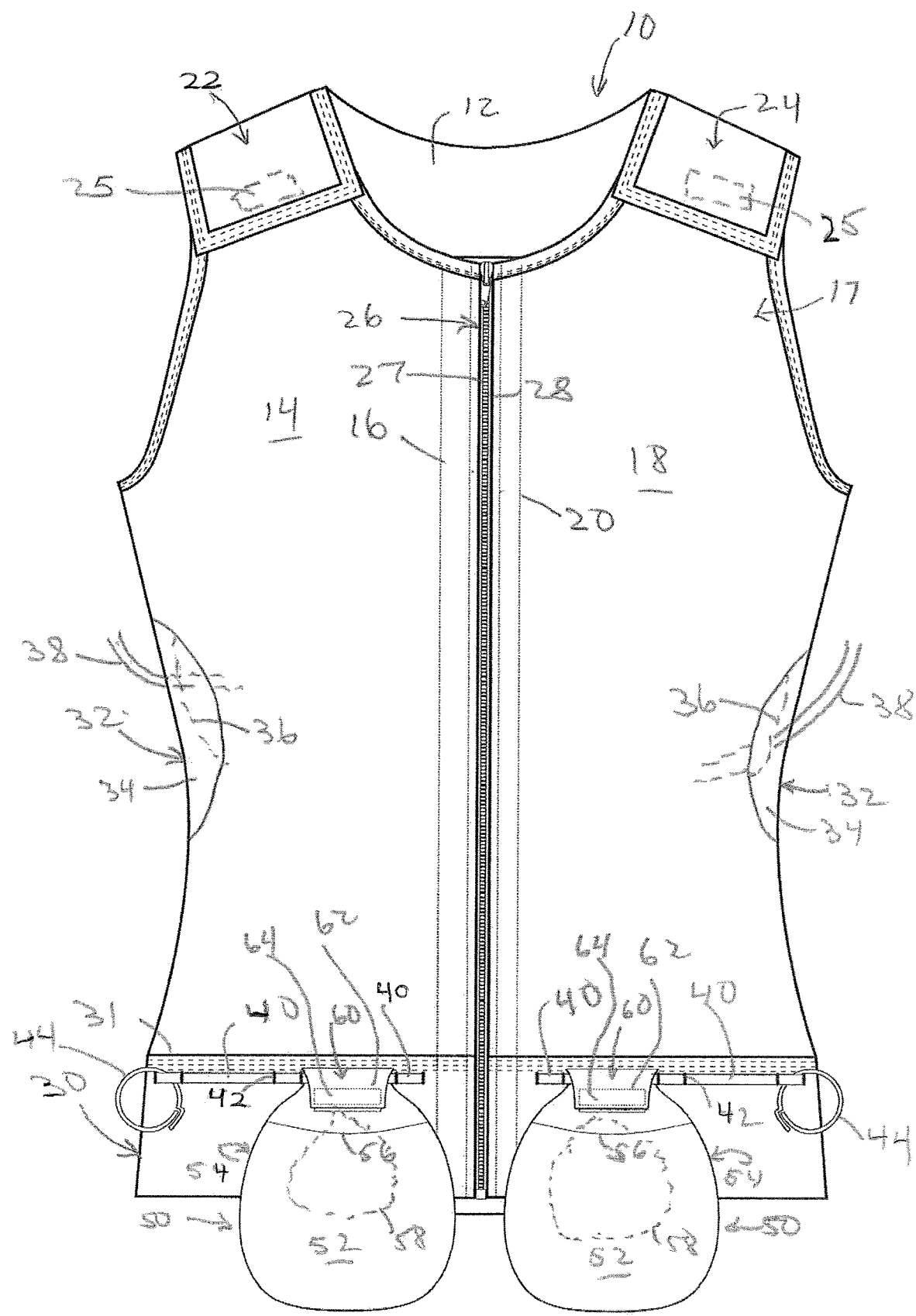
FIG. 1 is a front elevational view of one exemplary embodiment of a vest garment according to the present disclosure.

FIG. 1 shows one exemplary embodiment of a vest garment 10 generally comprising a rear fabric portion 12, a first front portion 14 having an edge 16 and a second front portion 18 having an edge 18. The rear portion 12 and front portions 14, 18 may be made of an elastic fabric. The vest includes an upper portion 17. In an exemplary embodiment, the fabric may be a compression fabric, such as, but not limited to, at least one warp knit compression fabric. In one exemplary embodiment, the fabric comprises a compression fabric having elasticity in the warp direction being substantially the same (e.g., within 10-20%) as the elasticity in the weft direction. In one exemplary embodiment, the fabric is COMFORTWEAR® brand fabric (available from The Marena Group, LLC, Lawrenceville, Ga.). In exemplary embodiments, at least a portion of the fabric comprising the vest may be treated with an anti-microbial agent for optimal healing. In exemplary embodiments, the anti-microbial agent may be Silvadur™ (available from Dow Chemical Company).

In exemplary embodiments, the vest 10 has a first shoulder strap 22 and a second shoulder strap 24. Each strap may have an adjustable strap closure 25, such as, but not limited to, a hook or a loop-type material, with a matable portion of the first and second front panel portions 14, 18 including a complementary loop or hook-type material. It is to be understood that other closure mechanisms may be used, such as, but not limited to, one or more buttons, snaps, or the like. In exemplary embodiments, the vest 10 has a front closure 26 comprising a first closure 27 portion and a second closure portion 28. The closure portions 26, 27 can be removably joined by one or more closure mechanisms, such as, but not limited to, a zipper, clasps, eye-and-hook, hook-and-loop, snaps, buttons, magnets, or the like. In exemplary embodiments, the closure mechanisms can be arranged in rows spaced generally from the top to the bottom of the front closure to permit adjusting the overall circumferential fit of the garment for different size wearers.

In exemplary embodiments, the vest 10 includes an elastic support band 30 proximate to the bottom 31 of the vest 10. The support band 30 assists in maintaining the vest 10 in place and is placed at the bottom 31 of the vest 10 to avoid sensitive healing areas after surgery. In exemplary embodiments, the support band 30 may be formed of a separate piece of elastic material and attached to the vest material. In exemplary embodiments, the support band 30 is sewn on top of the outside of the vest fabric to prevent or reduce irritation of scars caused by surgery. In exemplary embodiments, the support band 30 may be made of a material with a higher elasticity than the vest panel 12, 14, 18 material so as to improve the ability of the bottom of the vest 10 to stay down and not slide or ride up on the user.

In exemplary embodiments, there is an opening 32 in one or both sides of the vest 10 by having overlapping pieces 36, 36 of fabric. The opening 32 can permit easy access to a drainage tube 38 while still maintaining integrity of the vest sides.

In exemplary embodiments, at least one retention strip 40 of material, and in exemplary embodiments, a plurality of strips are attached to the support band 30. In exemplary embodiments, at least one of the strips 40 may be made of an elastic material. In other exemplary embodiments, the strips 40 are made of a relatively inelastic or less elastic material. Where a plurality of elastic strips are utilized, the elastic strips may be attached at spaced apart locations, such as by tack stitches 42. FIG. 1 shows a portion of an elastic strip 40 on each side of the front closure 26, whereby the elastic strip 40 is attached in various locations to the support band 30 to create a plurality of retention areas for attachment. In other exemplary embodiments, a plurality of separate strips 40 can be used. In exemplary embodiments, one or more elastic strips 40 and one or more relatively inelastic strips may be used. For the purposes of exemplary illustration, but not by way of limitation, a strip 40 of elastic material on each side of the closure will be described.

One or more retention members 44 can be attached to an elastic strip 40 at any of various locations. In exemplary embodiments the retention member 40 can be a ring (as shown in FIG. 1), such as, but not limited to, a split ring which can be removably associated with the elastic strip 40. In exemplary embodiments, instead of a ring, a clip, a loop of fabric having a snap, button, hook-and-loop, or other closure mechanism, can be used. In exemplary embodiments, the retention member 44 can be loop of fabric that is adjustably movable along the elastic strip 40, but is not removable.

In an alternative exemplary embodiment, the at least one elastic strip 40 may be attached to the vest below the support band 30, rather than being attached to the support band 30, such as being attached at an area proximate to the bottom 31 of the vest 10.

One or more pouches 50 can be attached to the vest 10. In exemplary embodiments, the pouch 50 can be removably attachable or associable with the vest 10. In exemplary embodiments, the pouch 50 comprises front and back fabric portions 52, 54 that are attached at the edges, and having an opening 56 into which a drainage bulb 58, cardiac monitor, or other item can be removably inserted. In exemplary embodiments, the pouch 50 can be removably attached to an elastic strip 40 by an attachment portion 60 having, in exemplary embodiments a strip of hook material 62 and a matable strip of loop material 64, each attached to the attachment portion 60. The attachment portion 60 can be folded over an elastic strip 40 and the hook and loop material 62, 64 mated to prevent removal until desired. The pouch 50 can be positioned at different places along an elastic strip 40 for easy adjustment.

In an alternative exemplary embodiment, the attachment portion 60 of the pouch 50 may have a strip of either hook material 62 or loop material 64 attached thereto, and the mating material can be attached to a portion of the support band 30, whereby the pouch 50 is directly attached to the support band 30. In alternative exemplary embodiments, other attachment mechanisms, such as, but not limited to, clasps, eye-and-hook, snaps, buttons, magnets, or the like, may be used.

One or more drainage assemblies commonly known in the art, such as, but not limited to a drainage tube 38 and drainage bulb 58, can be conveniently and comfortably used by having the drainage tube 38 extend from the wound area (e.g., chest), pass through (or be retained by) a retention member 44 and attach to a drainage bulb 58 removably contained in a pouch 50. Alternatively (or contemporaneously with the drainage assembly) a heart monitor and leads can be worn by having the leads retained by the retention member(s) 44 and the monitor being held by a pouch 50.

A wearer can wear the vest 10 with or without the pouch 50 and with or without the retention members 44.

A feature of exemplary embodiments of the vest 10 is that the retention members 44 can be removed, or can be moved to different locations along the elastic strip(s) 40 positioned around the support band 30 and generally maintained in place (within the elastic strip segment between two adjacent tack stitches 42) so that the wearer can position the drainage tube or tubes 38 in a comfortable location. Another feature of exemplary embodiments of the vest 10 is that the pouch 50 can be attached to the vest 10 at different locations, or removed from the vest 10, for greater comfort.

A feature of the embodiments of the present disclosure is that the compression aspect can help reduce post-surgical pain, prevent or reduce the likelihood of necrosis, as well as to promote healing of the wound. A feature of the garments of the present disclosure is that the drainage tube and bulb can be worn by the user in a more comfortable manner because the position of the tube and bulb can be adjusted, such as from the side to the front, depending on the activity or position of the user. A feature of the garments of the present disclosure is that the retention members 44 and/or the pouch 50 can be removed when not needed or when the garment is being laundered.

Figure 2:
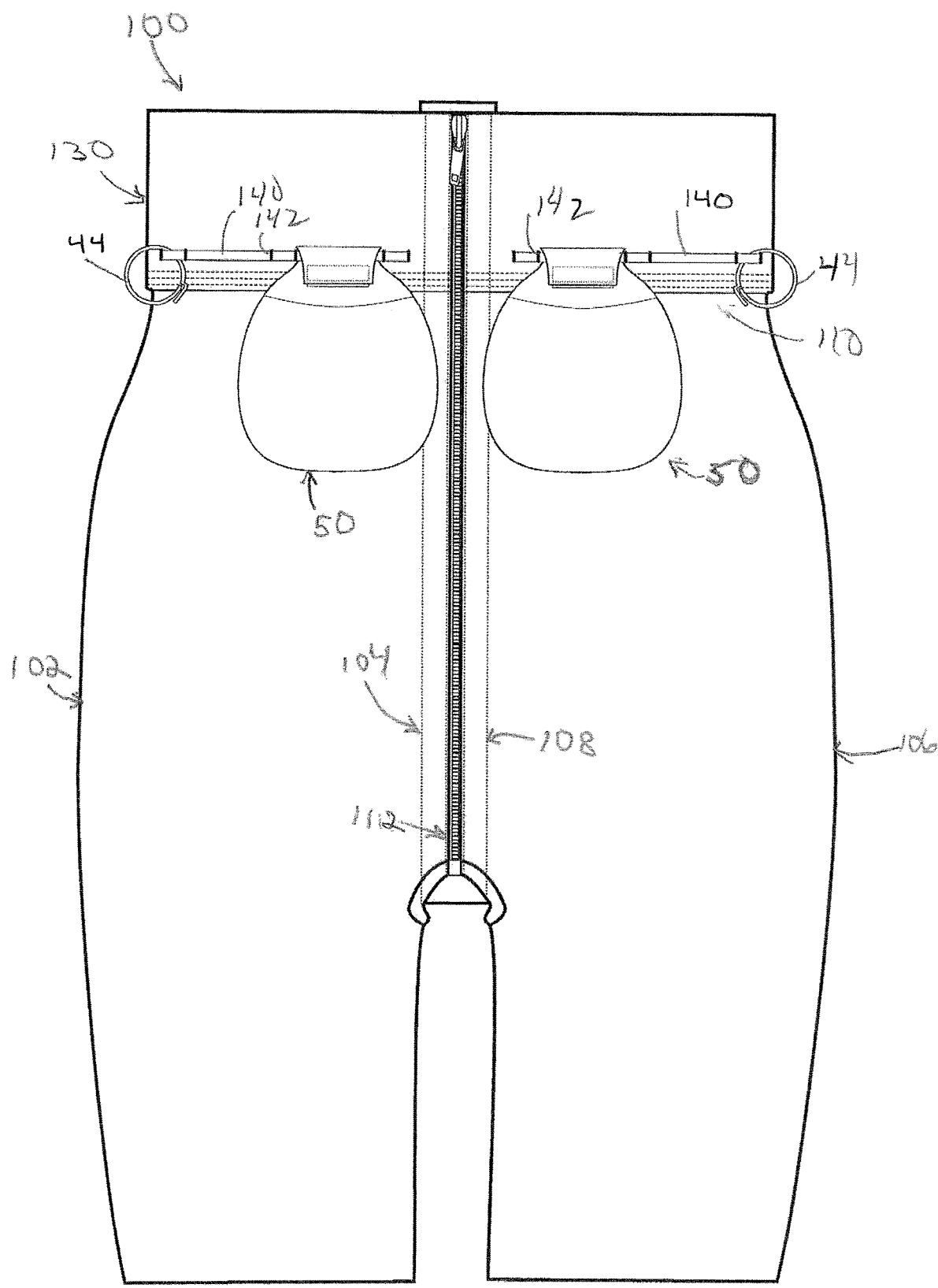
FIG. 2 is a front elevational view of a second exemplary embodiment of a waist cincher garment according to the present disclosure

In a second exemplary embodiment, shown in FIG. 2, a waist cincher garment 100 is provided having a construction analogous to the embodiments of FIG. 1 described hereinabove, but, rather than having shoulder straps, has a wider top edge that is generally positioned near the sternum area. The waist cincher garment may be used, for example, after hernia surgery. In exemplary embodiments, the garment 100 has a first portion 102 having an edge 104, and a second portion 106 having an edge 108 constructed of a fabric similar to the rear portion 10 and front portions 14, 18 described hereinabove. The garment 100 has an upper portion 110. A closure 112 can detachably associate the edges 104, 108 with each other. The closure 112 may be constructed similar to the front closure 26.

In this second exemplary embodiment, a support band 130, constructed similar to that of the support band 30, is attached to or otherwise associated with the upper portion 110 of the garment 100. One or more strips 140, similar to the strip 40, is associated with the support band 130, including, but not limited to, by tack stitches 142. One or more retention member 44 may be associated with the strip 140. In exemplary embodiments, one or more pouches 50 may be associated with the strip 140. The garment 100 is adapted to be wearable as an undergarment over at least a portion of a wearer's hips and thighs.

Figure 3:
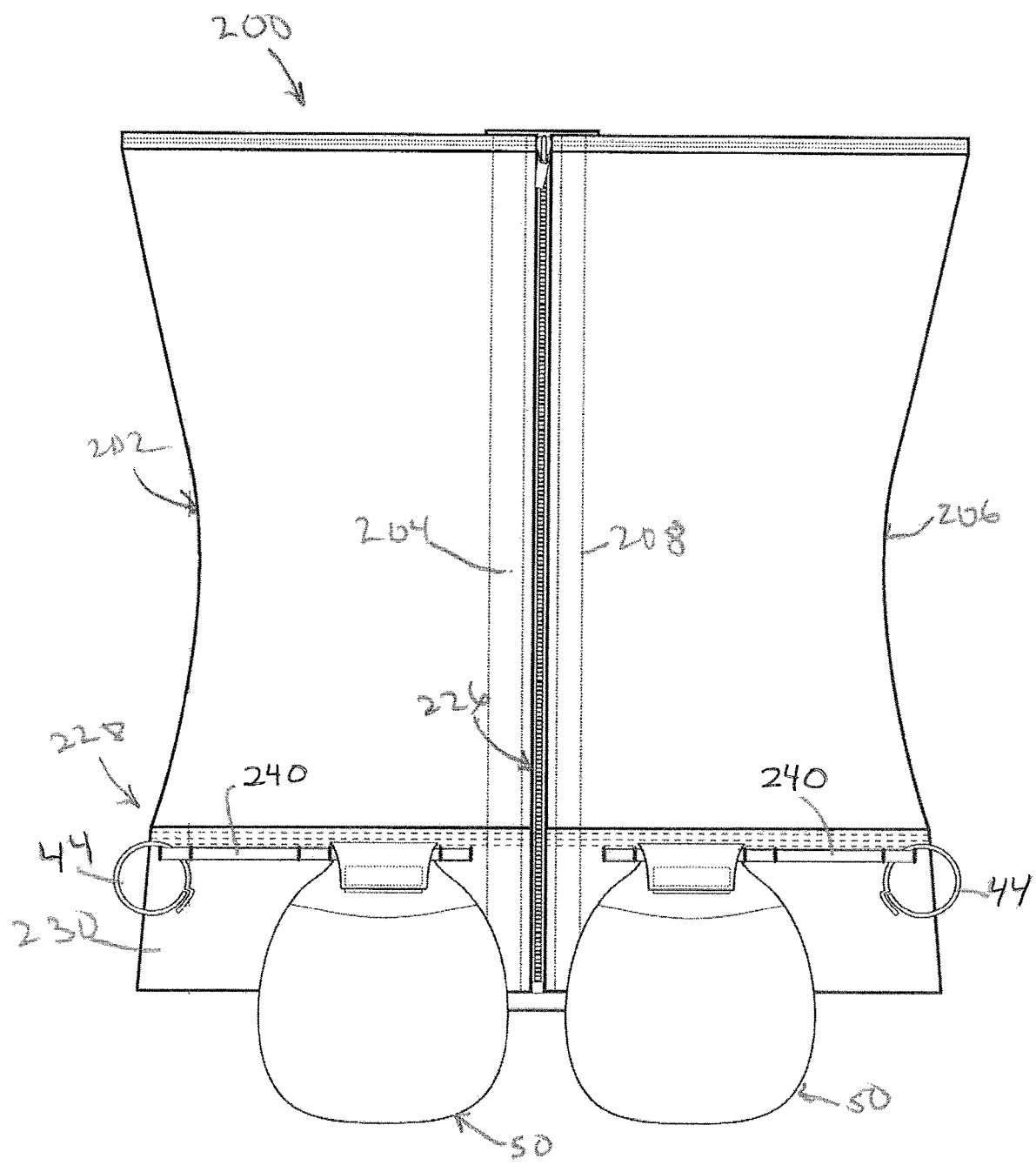
FIG. 3 is a front elevational view of a third exemplary embodiment of a girdle garment according to the present disclosure.

In a third exemplary embodiment, shown in FIG. 3, a girdle garment 200 is provided a having a first side panel 202 having an edge 204, and a second side panel 206 having an edge 208. The edges 204, 208 can be removably joined by a closure mechanism 226, similar to that described hereinabove with respect to the embodiments relating to FIG. 1. The girdle garment 200 has a bottom portion 228 having a support band 230 (similar to that described hereinabove) associated therewith. One or more strips 240 may be associated with the support band 230, as described hereinabove. At least one retention member 44 may be associable with one or more strips 240. Similarly, one or more pouches 50 can be removably (or nonremovably) associated with the one or more strips 240.

Figures 4, 5:
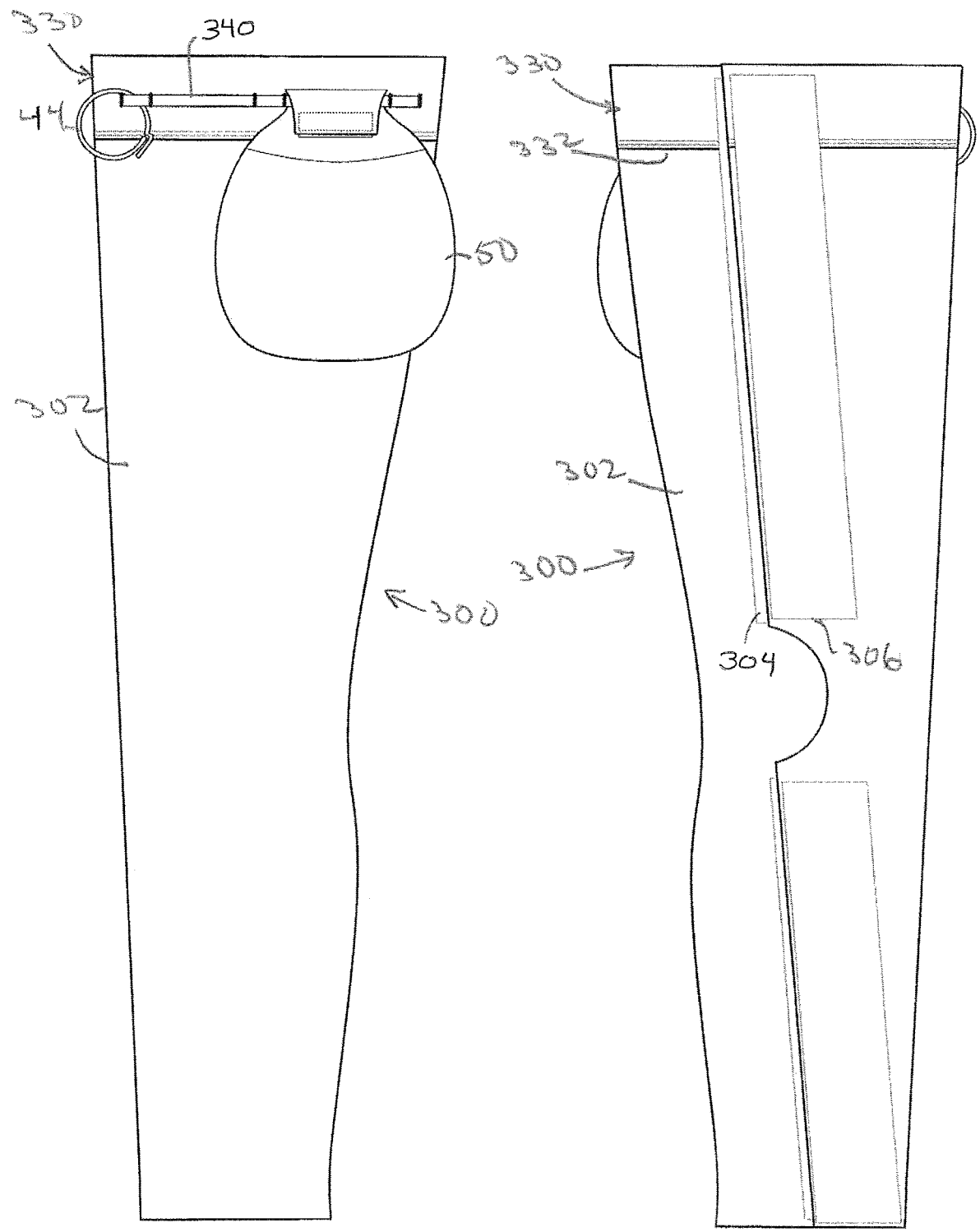
FIG. 4 is a front elevational view of a fourth exemplary embodiment of a leg sleeve garment according to the present disclosure.
FIG. 5 is a side elevational view of the embodiment of FIG. 4.

In a fourth exemplary embodiment, shown in FIGS. 4-5, a leg sleeve garment 300 is provided comprising a sleeve 302 of an elastic material similar to that described hereinabove. In exemplary embodiments, the leg sleeve 300 may have side edges 304, 306 that are joinable by a closure mechanism 326. In alternative exemplary embodiments, the sleeve 302 may not include a closure mechanism and can be a continuous sleeve of material that is slid over the user's leg. A support band 330 is associated with a top portion 332 of the sleeve 302 and may be positioned so as to be worn proximate to the user's waist area. Similar to the embodiments described hereinabove, one or more strips 340, retention members 44, and/or pouches 50 are included. The length of the leg sleeve 302 can be adapted to extend substantially the entire length of the leg from waist to calf, or can be shorter.

While exemplary embodiments of the present disclosure have been described in terms of a vest, waist cincher, girdle, or leg sleeve form, it is intended that the presently disclosed garment can be formed as other forms or structures.

The following numbered clauses include embodiments that are contemplated and non-limiting.

Clause 1: A garment for post-surgical use in pain and wound management, comprising: (a) a first panel portion including an edge, a second panel portion including an edge, the first and second panel portions having an upper portion and a bottom portion, the first and second panel portions being made of an elastic material; (b) a front closure adapted for removably joining at least a portion of the first and second panel portion edges; (c) an elastic support band associated with either the upper portion or the bottom portion; and, (d) at least one retention strip associated with the support band.

Clause 2: The garment of Clause 1, further comprising at least one retention member removably attachable to a portion of the at least one retention strip.

Clause 3: The garment of Clause 1, wherein the at least one retention strip is attached to the support band by a plurality of spaced apart tack stitches so as to form a plurality of retention areas.

Clause 4: The garment of Clause 1, further comprising at least one pouch adapted to be removably associated with a portion of the at least one strip.

Clause 5: The garment of Clause 2, wherein the at least one retention member is at least one split ring.

Clause 6: The garment of Clause 1, wherein at least one of the first panel portion or second panel portion further comprises an opening defined therein.

Clause 7: The garment of Clause 1, wherein the first panel portion further comprises a shoulder strap, and wherein the second panel portion further comprises a shoulder strap.

Clause 8: The garment of Clause 1, wherein the first panel portion and second panel portion form a girdle adapted to be worn over at least a portion of a wearer's torso.

Clause 9: The garment of Clause 1, wherein the first panel portion and second panel portion form a sleeve adapted to be worn over at least a portion of a wearer's leg.

Clause 10: The garment of Clause 1, wherein the first panel portion and second panel portion form an undergarment adapted to be worn over at least a portion of a wearer's hips and thighs.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

As used in the specification and the appended claims, the singular forms "a," "an" and "the" include plural referents unless the context clearly dictates otherwise.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

What is claimed is:

1. A garment for post-surgical use in pain and wound management, comprising:

a) a first panel portion including an edge, a second panel portion including an edge, the first and second panel portions having an upper portion and a bottom portion, the first and second panel portions being made of an elastic material;
b) a front closure adapted for removably joining at least a portion of the first and second panel portion edges;
c) an elastic support band coupled to either the upper portion or the bottom portion;
d) at least one retention strip coupled to the support band, the at least one retention strip configured to provide a plurality of attachment areas around the support band;
e) at least one retention member removably attachable to the attachment areas of the at least one retention strip and configured to support a drainage tube relative to the support band; and,
f) at least one pouch removably attachable to the attachment areas of the at least one strip and configured to support a drainage bulb relative to the support band,
wherein a plurality of tack stitches are formed across the at least one retention strip and define the plurality of attachment areas, the plurality of tack stitches separate adjacent attachment areas of the plurality of attachment areas, the at least one retention member is configured to be removed from one of the attachment areas and attached to another of the attachment areas at the selection of a user, the pouch is configured to be removed from one of the attachment areas and attached to another of the attachment areas at the selection of the user, and the plurality of tack stitches are configured to block movement of the at least one retention member along the at least one retention strip from one of the attachment areas to another of the attachment areas.

2. The garment of claim 1, wherein the at least one retention member is at least one split ring.

3. The garment of claim 1, wherein at least one of the first panel portion or second panel portion further comprises an opening defined therein.

4. The garment of claim 1, wherein the first panel portion further comprises a shoulder strap, and wherein the second panel portion further comprises a shoulder strap.

5. The garment of claim 1, wherein the first panel portion and second panel portion form a girdle adapted to be worn over at least a portion of the user's torso.

6. The garment of claim 1, wherein the first panel portion and second panel portion form a sleeve adapted to be worn over at least a portion of the user's leg.

7. The garment of claim 1, wherein the first panel portion and second panel portion form an undergarment adapted to be worn over at least a portion of the user's hips and thighs.

8. The garment of claim 1, wherein the plurality of tack stitches are configured to block movement of the pouch along the at least one retention strip from one of the attachment areas to another of the attachment areas.

9. The garment of claim 1, wherein adjacent tack stitches of the plurality of tack stiches maintain the pouch within one of the attachment areas defined by the adjacent tack stitches to which the pouch is attached.

10. The garment of claim 1, wherein the plurality of tack stitches attach the at least one retention strip to the elastic support band to define the plurality of attachment areas.

11. The garment of claim 1, wherein the plurality of attachment areas includes a first plurality of attachment areas arranged adjacent to the first panel portion and a second plurality of attachment areas arranged adjacent to the second panel portion.

12. The garment of claim 11, wherein the first plurality of attachment areas is separated from the second plurality of attachment areas by the front closure.

13. A garment for post-surgical use in pain and wound management, comprising:
a) a first panel portion, a second panel portion, the first and second panel portions having an upper portion and a bottom portion, the first and second panel portions being made of an elastic material;
b) a closure adapted for removably joining at least a portion of the first and second panel portions;
c) an elastic support band coupled to either the upper portion or the bottom portion;
d) a retention strip coupled to the support band, the retention strip configured to provide a plurality of attachment areas at least partially around the support band, wherein the retention strip is attached to the support band by a plurality of spaced apart tack stitches so as to form the plurality of attachment areas;
e) a retention member removably attachable to the attachment areas of the retention strip and configured to support a drainage tube relative to the support band; and,
f) a pouch removably attachable to the attachment areas of the retention strip and configured to support a drainage bulb relative to the support band,
wherein a plurality of tack stitches are formed across the at least one retention strip and define first, second, third, and fourth attachment areas, the plurality of tack stitches separate the first, second, third, and fourth attachment areas from one another, the at least one retention member is configured to be removed from the first attachment area and attached to the second attachment area at the selection of a user, the pouch is configured to be removed from the third attachment area and attached to the fourth attachment area at the selection of the user, and the plurality of tack stitches are configured to block movement of the at least one retention member along the at least one retention strip from the first attachment area to the second attachment area.

14. The garment of claim 13, wherein the plurality of attachment areas includes a first plurality of attachment areas arranged adjacent to the first panel portion and a second plurality of attachment areas arranged adjacent to the second panel portion.

15. The garment of claim 13, wherein the plurality of tack stitches attach the at least one retention strip to the elastic support band to define the plurality of attachment areas.

16. A garment for post-surgical use in pain and wound management, comprising:
a) a first panel portion including an edge, a second panel portion including an edge, the first and second panel portions having an upper portion and a bottom portion, the first and second panel portions being made of an elastic material;
b) a front closure adapted for removably joining at least a portion of the first and second panel portion edges;
c) an elastic support band coupled to either the upper portion or the bottom portion;
d) at least one retention strip coupled to the support band, the at least one retention strip configured to provide a plurality of attachment areas around the support band;
e) at least one retention member removably attachable to the attachment areas of the at least one retention strip and configured to support a drainage tube relative to the support band; and,
f) at least one pouch removably attachable to the attachment areas of the at least one strip and configured to support a drainage bulb relative to the support band, wherein a plurality of tack stitches are formed across the at least one retention strip and define the plurality of attachment areas, the plurality of tack stitches separate adjacent attachment areas of the plurality of attachment areas, the at least one retention member is configured to be removed from one of the attachment areas and attached to another of the attachment areas at the selection of a user, and the pouch is configured to be removed from one of the attachment areas and attached to another of the attachment areas at the selection of the user, and adjacent tack stitches of the plurality of tack stiches maintain the at least one retention member within one of the attachment areas defined by the adjacent tack stitches to which the at least one retention member is attached.

* * * * *